(12) United States Patent  
Klich

(10) Patent No.: US 6,736,135 B1
(45) Date of Patent: May 18, 2004

(54) NEBULIZER PUMP ADAPTER

(76) Inventor: John D. Klich, 307-1619 Lawrence Avenue West, Toronto, ON (CA), M6L 1C3

( * ) Notice: Subject to any disclaimer, the term of this patent is extended or adjusted under 35 U.S.C. 154(b) by 45 days.

(21) Appl. No.: 10/174,311

(22) Filed: Jun. 17, 2002

(51) Int. Cl.[7] .............................................. A61M 11/00
(52) U.S. Cl. ........................... 128/200.14; 128/200.16; 128/200.18; 128/200.21; 128/200.23; 128/204.21; 55/385.1; 55/385.4; 239/338
(58) Field of Search .............................. 55/385.1, 385.4; 128/200.14, 200.16, 200.18, 200.21, 200.23, 204.21; 239/338

(56) References Cited

U.S. PATENT DOCUMENTS 3,002,870 A * 10/1961 Belgarde et al. .............. 156/70
5,203,506 A * 4/1993 Gross et al. ................. 239/224
5,277,175 A * 1/1994 Riggs et al. ........... 128/200.21
6,578,224 B1 * 6/2003 Lawson et al. ............. 239/337
6,615,824 B2 * 9/2003 Power ................... 128/200.14

* cited by examiner

Primary Examiner—Minh-Chau T. Pham

(57) ABSTRACT

Nebulizer pump adapters allow the attachment of a bicycle pump to a nebulizer when a source of compressed air is not otherwise available. In order for a nebulizer to work, there must be a source of gas flow sufficient to nebulize the solution. The compressed gas tank or electrical air compressor that is normally used may not be available in certain situations, such as in the wilderness or during a blackout. As a result, having the option of using a hand-operated pump may be critical in administering inhaled aerosol medications.

18 Claims, 2 Drawing Sheets

NEBULIZER PUMP ADAPTER

BACKGROUND OF THE INVENTION

1. Field of the Invention

Figure 1:
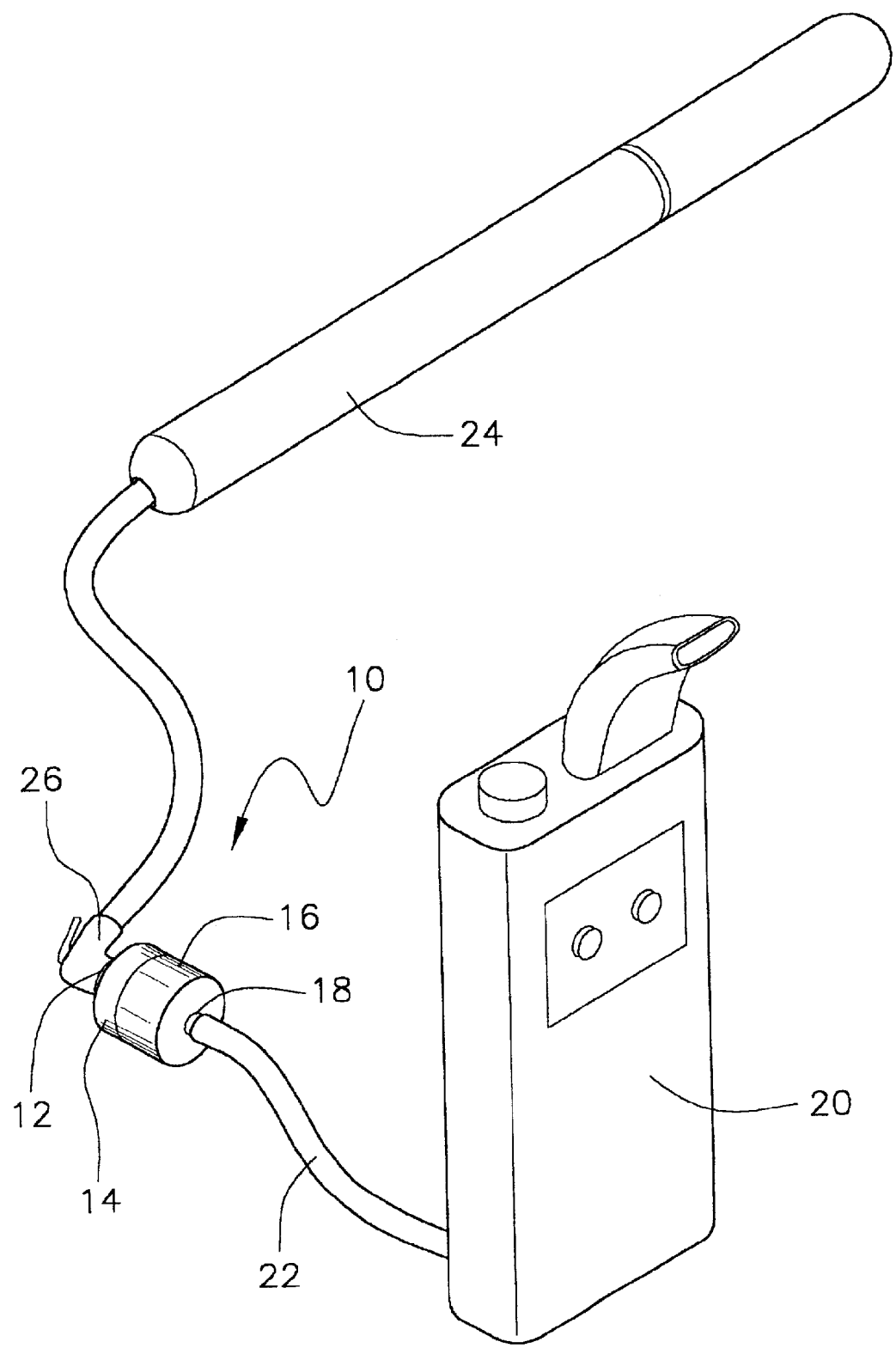
Figure 2:
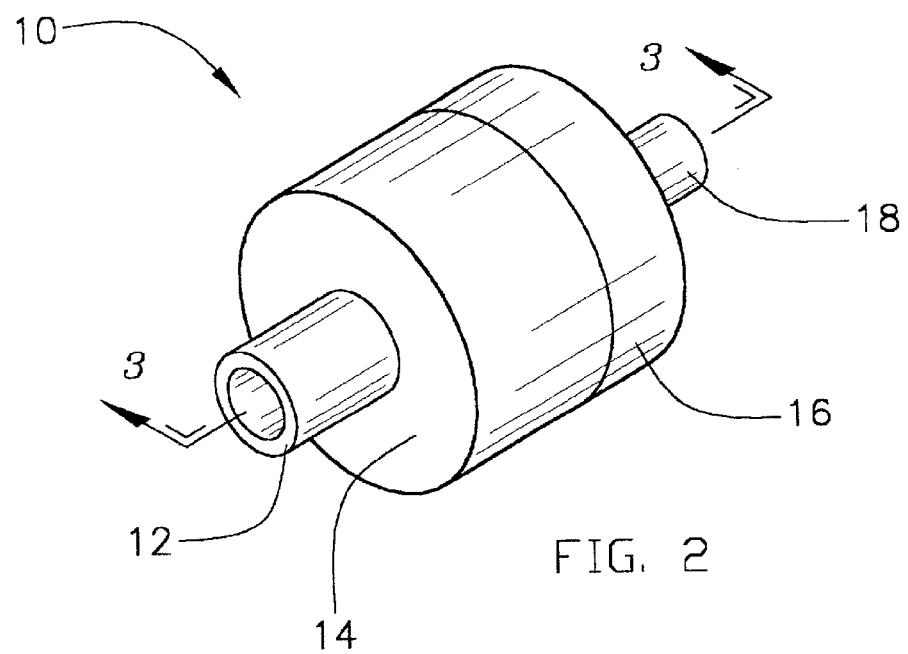
Figure 3:
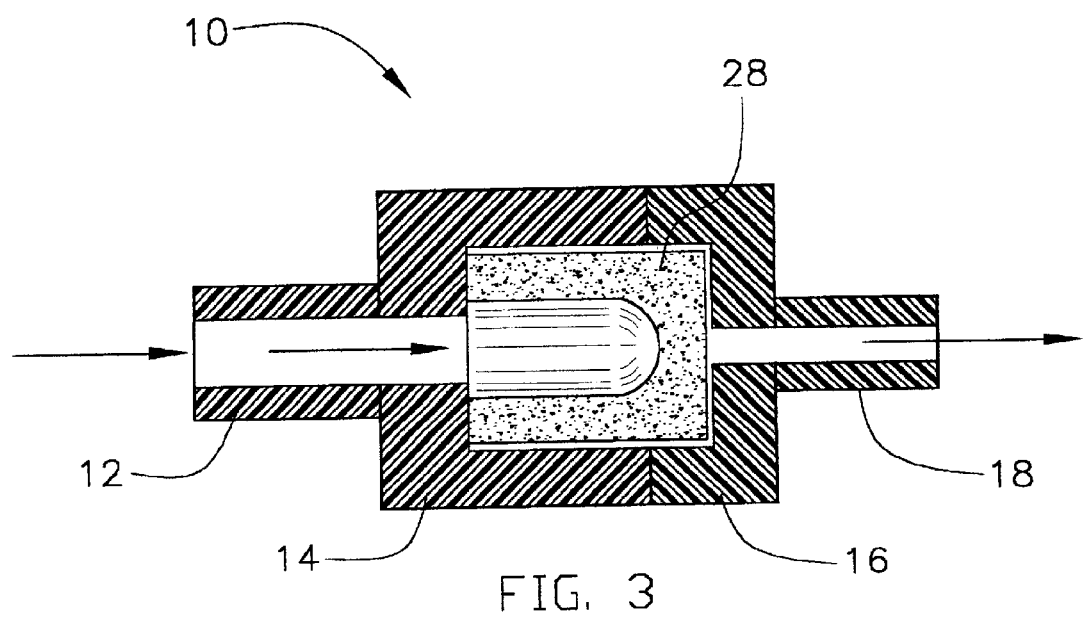

The present invention relates to a nebulizer pump adapter for use in connection with nebulizers. The nebulizer pump adapter has particular utility in connection with providing a source of gas flow when a compressed gas tank or electrical air compressor is not available.

2. Description of the Prior Art

Nebulizer pump adapters are desirable for allowing the attachment of a bicycle pump to a nebulizer when a source of compressed air is not otherwise available. In order for a nebulizer to work, there must be a source of gas flow sufficient to nebulize the solution. The compressed gas tank or electrical air compressor which is normally used may not be available in certain situations, such as in the wilderness or during a blackout. As a result, having the option of using a hand-operated pump may be critical in administering inhaled aerosol medications.

The use of nebulizer bacteria filters is known in the prior art. For example, U.S. Pat. No. 3,932,153 to Byrns discloses a nebulizer bacteria filter. However, the Byrns '153 patent does not have a Schrader valve-sized pump connector, and has further drawbacks of not having a hollow cylindrical filter with a beveled bottom.

U.S. Pat. No. 5,776,342 to Hiranaga et al. discloses a filter assembly that provides increased strength. However, the Hiranaga et al. '342 patent does not have a Schrader valve-sized pump connector, and additionally does not have a hollow cylindrical filter with a beveled bottom.

Similarly, U.S. Pat. No. 5,195,527 to Hicks discloses respiratory filters that are included in a respiratory system used in anesthesia and/or patient ventilation. However, the Hicks '527 patent does not have a Schrader valve-sized pump connector, and also lacks a hollow cylindrical filter with a beveled bottom.

In addition, U.S. Pat. No. 4,148,732 to Burrow et al. discloses a bacteria filter unit that comprises a two-piece molded housing. However, the Burrow et al. '732 patent does not have a Schrader valve-sized pump connector, and also does not have a hollow cylindrical filter with a beveled bottom.

Furthermore, U.S. Pat. No. 4,444,661 to Jackson et al. discloses a filter device that has a plastic housing with inlet and outlet chambers separated by a filter disc. However, the Jackson et al. '661 patent does not have a Schrader valve-sized pump connector, and further lacks a hollow cylindrical filter with a beveled bottom.

Lastly, U.S. Pat. No. 5,230,727 to Pound et al. discloses an air filter for medical ventilation equipment and the like that is an inexpensive, bidirectional, low flow resistance air filter. However, the Pound et al. '727 patent does not have a Schrader valve-sized pump connector, and has the additional deficiency of not having a hollow cylindrical filter with a beveled bottom.

While the above-described devices fulfill their respective, particular objectives and requirements, the aforementioned patents do not describe a nebulizer pump adapter that allows providing a source of gas flow when a compressed gas tank or electrical air compressor is not available. The above patents make no provision for connecting a Schrader valve-sized pump to the filtering apparatus. Furthermore, none of the above patents have a hollow cylindrical filter with a beveled bottom.

Therefore, a need exists for a new and improved nebulizer pump adapter that can be used for providing a source of gas flow when a compressed gas tank or electrical air compressor is not available. In this regard, the present invention substantially fulfills this need. In this respect, the nebulizer pump adapter according to the present invention substantially departs from the conventional concepts and designs of the prior art, and in doing so provides an apparatus primarily developed for the purpose of providing a source of gas flow when a compressed gas tank or electrical air compressor is not available.

SUMMARY OF THE INVENTION

In view of the foregoing disadvantages inherent in the known types of nebulizer bacteria filters now present in the prior art, the present invention provides an improved nebulizer pump adapter, and overcomes the above-mentioned disadvantages and drawbacks of the prior art. As such, the general purpose of the present invention, which will be described subsequently in greater detail, is to provide a new and improved nebulizer pump adapter which has all the advantages of the prior art mentioned heretofore and many novel features that result in a nebulizer pump adapter which is not anticipated, rendered obvious, suggested, or even implied by the prior art, either alone or in any combination thereof.

To attain this, the present invention essentially comprises a hollow pump connection and a hollow tubing connection removably attached to the pump connection. An additional significant element is a hollow cylindrical filter with a beveled bottom housed within the hollow pump connection and hollow tubing connection.

There has thus been outlined, rather broadly, the more important features of the invention in order that the detailed description thereof that follows may be better understood and in order that the present contribution to the art may be better appreciated. The invention may also include the hollow pump connection having a hollow pump connector which is sized to accept a Schrader valve-sized pump. The hollow tubing connection may have a hollow tubing connector sized to accept nebulizer tubing. The hollow pump connection may also be permanently attached to the hollow tubing connection. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently current, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved nebulizer pump adapter that has all of the advantages of the prior art nebulizer bacteria filters and none of the disadvantages.

It is another object of the present invention to provide a new and improved nebulizer pump adapter that may be easily and efficiently manufactured and marketed.

An even further object of the present invention is to provide a new and improved nebulizer pump adapter that has a low cost of manufacture with regard to both materials and labor, and which accordingly is then susceptible of low prices of sale to the consuming public, thereby making such nebulizer pump adapter economically available to the buying public.

Still another object of the present invention is to provide a new nebulizer pump adapter that provides in the apparatuses and methods of the prior art some of the advantages thereof, while simultaneously overcoming some of the disadvantages normally associated therewith.

Even still another object of the present invention is to provide a nebulizer pump adapter for providing a source of gas flow when a compressed gas tank or electrical air compressor is not available. This allows the use of a hand-operated pump, such as a bicycle pump, to operate a nebulizer.

Still yet another object of the present invention is to provide a nebulizer pump adapter for providing a source of gas flow when a compressed gas tank or electrical air compressor is not available. This makes it possible to administer aerosol medication from a nebulizer under almost any circumstances.

An additional object of the present invention is to provide a nebulizer pump adapter for providing a source of gas flow when a compressed gas tank or electrical air compressor is not available. This ensures that the air entering the nebulizer is not contaminated.

A further object of the present invention is to provide a nebulizer pump adapter for providing a source of gas flow when a compressed gas tank or electrical air compressor is not available. This makes it possible to change the filter while reusing the other parts of the nebulizer pump adapter.

Lastly, it is an object of the present invention to provide a new and improved nebulizer pump adapter for providing a source of gas flow when a compressed gas tank or electrical air compressor is not available.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated current embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a top perspective view of the current embodiment of the nebulizer pump adapter constructed in accordance with the principles of the present invention.

FIG. 2 is a top perspective view of the nebulizer pump adapter of the present invention.

FIG. 3 is a side sectional view of the nebulizer pump adapter of the present invention.

The same reference numerals refer to the same parts throughout the various figures.

DESCRIPTION OF THE CURRENT EMBODIMENT

Referring now to the drawings, and particularly to FIGS. 1–3, a current embodiment of the nebulizer pump adapter of the present invention is shown and generally designated by the reference numeral 10.

In FIG. 1, a new and improved nebulizer pump adapter 10 of the present invention for providing a source of gas flow when a compressed gas tank or electrical air compressor is not available is illustrated and will be described. More particularly, the nebulizer pump adapter 10 has a hollow pump connector 12 sized to fit a Schrader valve connector 26 attached to pump 24. In the current embodiment, pump connector 12 is made of plastic. Pump connector 12 is molded to hollow front cylinder 14, also made of plastic. Threadedly connected to front cylinder 14 is hollow rear cylinder 16 made of plastic. Molded to rear cylinder 16 is hollow tubing connector 18 which is sized to fit nebulizer tubing. In the current embodiment, tubing connector 18 is made of plastic. Tubing 22 is shown connecting nebulizer 20 with nebulizer pump adapter 10. Note that the pump 24, Schrader valve connector 26, tubing 22, and nebulizer 20 are for illustrative purposes only and are not part of the current invention.

Moving on to FIG. 2, a new and improved nebulizer pump adapter 10 of the present invention for providing a source of gas flow when a compressed gas tank or electrical air compressor is not available is illustrated and will be described. More particularly, the nebulizer pump adapter 10 has a pump connector 12 molded to front cylinder 14. Front cylinder 14 is threadedly attached to rear cylinder 16. Tubing connector 18 is molded to rear cylinder 16.

Concluding with FIG. 3, a new and improved nebulizer pump adapter 10 of the present invention for providing a source of gas flow when a compressed gas tank or electrical air compressor is not available is illustrated and will be described. More particularly, the nebulizer pump adapter 10 has a pump connector 12 molded to front cylinder 14. Front cylinder 14 is threadedly attached to rear cylinder 16. Tubing connector 18 is molded to rear cylinder 16. Enclosed by front cylinder 14 and rear cylinder 16 is filter 28 made of corrugated paper. Filter 28 is hollow and has a beveled bottom. This shape forms an enhanced surface area profile to improve filtration efficiency.

In use, it can now be understood that a source of compressed air, such as a pump 24, is attached to pump connector 12. Upon activation of the pump 24, compressed air flows through Schrader valve connector 26 into pump connector 12. From pump connector 12, the gas flows into front cylinder 14. The gas is filtered as it passes through filter 28 and enters rear cylinder 16. From rear cylinder 16, the gas flows into tubing 22, and from there to nebulizer 20.

While a current embodiment of the nebulizer pump adapter has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy material such as stainless steel, aluminum, or titanium may be used instead of the plastic pump connector, front cylinder, rear cylinder, and tubing connector described. Also, the corrugated paper filter may also be made of organic porous films made of polyolefin, nylon, or fluorocarbon resin. And although providing a source of gas flow when a compressed gas tank or electrical air compressor is not available has been described, it should be appreciated that the nebulizer pump adapter herein described is also suitable for filtering gases and liquids in a variety of other applications. Furthermore, a wide variety of pumps may be used instead of the Schrader valve-sized pump described Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A nebulizer pump adapter comprising:

a hollow pump connection, wherein said pump connection is sized to fit the Schrader valve-sized connector of a manually operated pump; and a hollow tubing connection removably attached to said pump connection.

2. The nebulizer pump adapter as defined in claim 1, wherein said pump connection comprises:

a hollow pump connector; and a hollow front cylinder attached to said hollow pump connector.

3. The nebulizer pump adapter as defined in claim 1, wherein said tubing connection comprises:

a hollow tubing connector; and a hollow rear cylinder attached to said hollow tubing connector.

4. The nebulizer pump adapter as defined in claim 1, wherein said pump connection is threadedly connected to said tubing connection.

5. The nebulizer pump adapter as defined in claim 1, wherein said pump connection is connected to said tubing connection by an interlocking flange.

6. The nebulizer pump adapter as defined in claim 3, wherein said hollow tubing connector is sized to fit the tubing used for nebulizers.

7. The nebulizer pump adapter as defined in claim 1, wherein said pump is selected from the group consisting of bicycle frame pumps, upright bicycle pumps, and foot-operated pumps.

8. The nebulizer pump adapter as defined in claim 1, further comprising a filter housed within said hollow pump connection and said hollow tubing connection.

9. The nebulizer pump adapter as defined in claim 8, wherein said filter is selected from the group consisting of corrugated paper and organic porous films made of polyolefin, nylon, or fluorocarbon resin.

10. The nebulizer pump adapter as defined in claim 8, wherein said filter has a hollow cylindrical shape open at one end with a beveled interior bottom.

11. The nebulizer pump adapter as defined in claim 1, wherein said pump connection is selected from the group consisting of stainless steel, plastic, aluminum, and titanium.

12. The nebulizer pump adapter as defined in claim 1, wherein said tubing connection is selected from the group consisting of stainless steel, plastic, aluminum, and titanium.

13. A nebulizer pump adapter comprising:

a hollow pump connection, wherein said pump connection is sized to fit the Presta valve-sized connector of a manually operated pump;

a hollow tubing connection attached to said pump connection using attachment means; and a filter housed within said hollow pump connection and said hollow tubing connection.

14. The nebulizer pump adapter as defined in claim 13, wherein said attachment means is selected from the group consisting of gluing, molding, and welding.

15. The nebulizer pump adapter as defined in claim 13, wherein said pump connection comprises:

a hollow pump connector; and a hollow front cylinder attached to said hollow pump connector.

16. The nebulizer pump adapter as defined in claim 13, wherein said tubing connection comprises:

a hollow tubing connector; and a hollow rear cylinder attached to said hollow tubing connector.

17. The filter as defined in claim 13, wherein said filter has a hollow cylindrical shape open at one end with a beveled interior bottom.

18. A nebulizer pump adapter comprising:

a hollow pump connector sized to fit the Schrader valve-sized connector of a manually operated pump, wherein said pump delivers air to, but does not withdraw air from, said nebulizer pump adapter;

a hollow front cylinder attached to said hollow pump connector;

a hollow rear cylinder attached to said hollow front cylinder;

a hollow tubing connector sized to fit the tubing used for nebulizers attached to said hollow rear cylinder; and a filter having a hollow cylindrical shape open at one end with a beveled interior bottom housed within said hollow pump connection and said hollow tubing connection.

* * * * *